Figure 1:
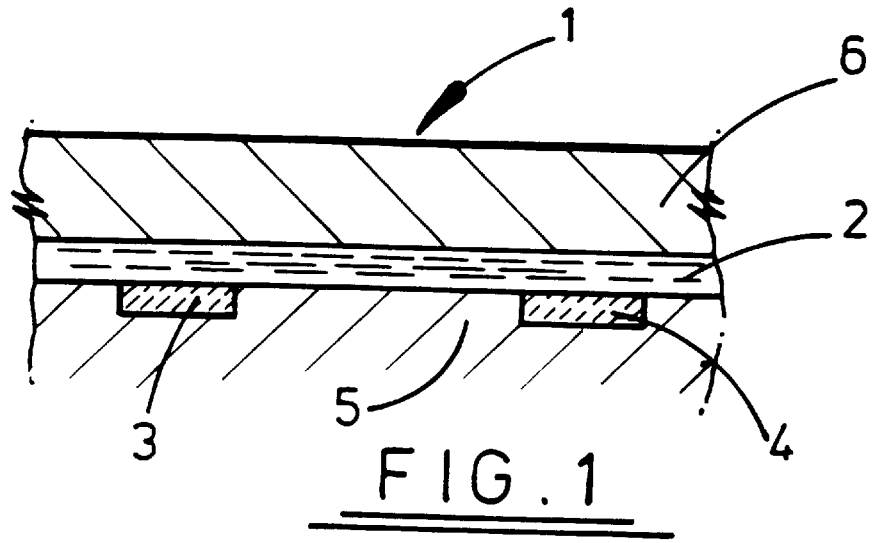

United States Patent [19]
Treloar et al.

[11] Patent Number: 5,906,719
[45] Date of Patent: May 25, 1999

[54] SENSOR DEVICE

[75] Inventors: Paul Howard Treloar, Chester; Ian Mcintyre Christie, Stockport; Pankaj Maganlal Vadgama, Manchester, all of United Kingdom

[73] Assignee: The Victoria University of Manchester, Manchester, United Kingdom

[21] Appl. No.: 08/682,540

[22] PCT Filed: Jan. 25, 1995

[86] PCT No.: PCT/GB95/00145

§ 371 Date: Oct. 16, 1996

§ 102(e) Date: Oct. 16, 1996

[87] PCT Pub. No.: WO95/20050

PCT Pub. Date: Jul. 27, 1995

[30] Foreign Application Priority Data

Jan. 25, 1994 [GB] United Kingdom .................... 9401356

[51] Int. Cl.⁶ .................................................. G01N 27/404
[52] U.S. Cl. .......................... 204/415; 204/403; 204/416;
204/418; 205/778; 205/779; 205/781.5;
205/782.5; 205/787; 205/789
[58] Field of Search ...................... 204/403, 415,
204/416, 418, 419; 205/778, 778.5, 779,
781.5, 782.5, 783, 789, 787

[56] References Cited

U.S. PATENT DOCUMENTS

| | | | |
|---|---|---|---|
| 2,913,386 | 11/1959 | Clark ........................................ | 204/415 |
| 3,700,579 | 10/1972 | Clifton et al. ............................ | 204/415 |
| 4,549,951 | 10/1985 | Knudson et al. ........................ | 204/418 |
| 4,571,293 | 2/1986 | Seshimoto et al. ...................... | 204/418 |
| 4,871,442 | 10/1989 | Yamaguchi et al. ..................... | 204/416 |
| 4,973,394 | 11/1990 | Ross et al. ............................... | 204/418 |
| 5,227,042 | 7/1993 | Zawodzinski et al. .................. | 204/418 |
| 5,421,983 | 6/1995 | Slack et al. .............................. | 204/418 |

FOREIGN PATENT DOCUMENTS

| | | |
|---|---|---|
| 0 138 150 A3 | 4/1985 | European Pat. Off. . |
| 0 221 508 A1 | 5/1987 | European Pat. Off. . |
| WO 92/16647 | 10/1992 | WIPO . |

OTHER PUBLICATIONS

I.M. Christie, P.H., Treloar and P. Vadgama, "Platicized poly(vinyl chloride) as a a permselective barrier membrane for high–selectively amperometric sensors and biosensors", Analytica Chimica Acta, vol. 269, 1992 month unavailable.

*Primary Examiner*—T. Dung
*Attorney, Agent, or Firm*—Woodard, Emhardt, Naughton Moriarty & McNett

[57] ABSTRACT

An amperometric sensor device comprising a working electrode, a reference/pseudo-reference electrode and a permselective membrane incorporating a charged organic species. The electrodes are in intimate contact with the membrane and are on a side of the membrane opposite to the side exposed to a fluid sample. The charged organic species provides a conducting path through the membrane between the electrodes.

10 Claims, 1 Drawing Sheet

SENSOR DEVICE

The present invention relates to sensor devices such as are used in the determination of a component or components which may be present in a fluid sample such as a physiological fluid (e.g. blood, urine) or an effluent.

PCT Application No. PCT/GB92/00443 (Publication No. WO-A-92/16647) discloses a sensor device which is suitable for detecting a targeted lipophilic component present in a fluid sample and providing an output representative of the content of the component in the sample. This device incorporates a permselective membrane which is substantially impermeable to charged non-lipophilic species that may be present in samples to be analysed and being selective, by partitioning, for lipophilic species. As a result, a preselected lipophilic component in the sample partitions into and diffuses through the barrier for detection on the other side thereof.

In preferred embodiments of the aforesaid PCT application the membrane is of PVC incorporating a plasticiser (which acts as a permselective medium) such as dioctylphthalate or iso-propyl myristate. Such membranes are preferably used in an amperometric sensor incorporating an electrochemical detection arrangement comprising an electrode system and a liquid or gel phase electrolyte medium which is interposed between the membrane and the electrodes. The electrode system may comprise a working electrode and a reference (or pseudo reference) electrode. The electrolyte medium provides a charge carrier system which ensures that a current may flow between the electrodes.

Whilst giving satisfactory results, the use of the electrolyte medium (which is usually, but not necessarily, aqueous) does however present a number of disadvantages. In particular it complicates cell construction and is not particularly suitable for use in dry reagent strip format sensors.

It is therefore an object of the present invention to obviate or mitigate the abovementioned disadvantages.

According to the present invention there is provided a sensor device for detecting a predetermined component present in a fluid sample and providing an output representative thereof, the device comprising a permselective membrane incorporating a charged organic species, said permselective membrane being at least partially impermeable to charged substantially non-lipophilic species that may be present in the sample, and an electrode arrangement in intimate contact with the membrane but not exposed at the side thereof to be presented to the fluid sample.

Therefore in accordance with the invention the permselective membrane incorporates a charged organic species (which may function as a charge carrier) and as such it is possible for the electrode arrangement to be in intimate contact with the membrane. The membrane therefore, combines both the functions of supporting electrolyte and permselective barrier. The need to provide a separate liquid or gel phase electrolyte medium between the electrodes and the membrane is thus avoided. This provides significant advantages including the possibility of highly simplified cell construction with no liquid reagents, such constructions being suitable in principle for dry reagent strip format sensors.

A further advantage associated with the use of the charged organic species is that organic phase electrochemistry can be exploited allowing a wider voltage range to be applied than can be used with aqueous electrolyte layers (due to the break down of water at high voltages).

The electrode arrangement may be in intimate contact with the face of the membrane opposite to that face which is presented to the sample. Alternatively the necessary intimate contact may be achieved by virtue of the electrodes being incorporated within the membrane without being exposed to the sample.

Sensor devices in accordance with the invention are preferably non-potentiometric devices. Most preferably the sensor devices are amperometric devices in which the electrode system comprises a working electrode and a reference or pseudo-reference electrode system. In operation of such devices, the working electrode is maintained at a predetermined potential with respect to the reference electrode. This potential is selected to discharge a species of interest at the working electrode resulting an electric current which can be measured.

Examples of suitable charged organic species for use in the invention include ion exchanges as used in ion selective electrodes (e.g. PVC based ion selective electrodes).

The charged organic species may comprise a positive or negative organic ion, associated in either case with an appropriate counter-ion (e.g. an inorganic ion). Alternatively the charged organic species may be zwitterionic. It is also to be understood that the term charged organic species covers organic species which, whilst not having a formal charge per se, are closely associated with a charged species for example, organic molecules having a cage structure in which an ion is incorporated are covered by the term 'charged organic species' as used herein. The hydrophobic nature of the membrane ensures that the charged organic species is retained therein.

Examples of charged organic carrier species having a positive organic ion are quaternary ammonium salts incorporating at least one, more preferably at least 2, and most preferably at least 3 long chain substituted or unsubstituted hydrocarbon groups having 6 or more carbon atoms. Thus for example these groups may be aliphatic chains with optional (e.g aromatic) substituents. Alternatively, there may be one or more aryl groups bonded directly to the quaternary nitrogen atom. The negative counter ion is preferably a simple inorganic ion, e.g. halide such as chloride.

A preferred example of positive organic ion for use in the invention is the tricaprylylmethyl ammonium ion.

Examples of charged organic species incorporating a negative organic ion include tetra-alkyl or tetra-aryl borates, e.g. a tetraphenyl borate. The counter ion may be a simple inorganic cation, e.g. an alkali metal cation. A preferred salt for use in the invention incorporating a negative organic ion is sodium tetraphenyl borate.

Further examples of charged organic species which may be used in accordance with the invention include di-(n-long chain alkyl) phosphates, e.g. provided as the calcium salts. Particular examples include calcium di-(n-decyl)phosphate, and calcium di(n-(1,1,3,3-tetramethylbutyl))phosphate, and bis(2-ethylhexyl)hydrogen phosphate in which the hydrogen ion can be replaced by metal ions, particularly calcium. A further example is ferroinalkylbenzene sulphonate. A further possibility is to use ionophores as pendant groups with chelated metal ions, or to use a redox active polymer or derivatives.

The charged organic species may be one which provides, or at least contributes to, the permselective properties of the membrane.

The presence of the charged species is likely to impart ion exchange properties. Hence the lipophilic selectivity of the membrane is likely to be reduced as compared to membranes as disclosed in WO-A-92/16647. Furthermore membranes as disclosed herein might be suitable for targeting non-lipophilic analytes, possibly charged.

The permselective membrane preferably comprises a synthetic polymer membrane incorporating the charged organic species. The polymer membrane is preferably plasticised, e.g. by virtue of the presence therein of the species used as the charged organic species or by additional plasticiser (e.g. dioctylphthalate).

The preferred polymer is PVC although other synthetic polymers may be used.

A membrane for use in the invention may be formulated by casting a solution (e.g. in THF) of the synthetic polymer (preferably PVC) and liquid tricapylylmethyl ammonium chloride (available under the name Aliquat 336), and allowing the solvent to evaporate. In this case the charged organic species functions both as plasticiser and charge carrier.

It is also possible for the charged organic species to be provided by a solid organic salt (e.g. sodium tetraphenyl borate). In this case, the solid salt together with the polymer may be dissolved in an organic liquid (e.g. isopropyl myristate) which acts as plasticiser during membrane fabrication.

The amount of charged organic species incorporated in the membrane will depend on the particular application. Additionally it should be noted that excess organic species may allow significant interference from permeating species facilitated by ion exchange properties of the organic species. In the case of a charged organic species which (with its counterion) is a liquid then generally less than 10 $\mu$l (e.g. 2–5 $\mu$l) of the liquid will be used per 1 mg of polymer powder (e.g. PVC used for fabricating the membrane. If the charged organic species (with its counterion) is a solid then generally a maximum of 35 mg of the solid will be used per 60 mg of polymer together with 2–5 $\mu$l of plasticiser per 1 mg of polymer. The amounts quoted as to be understood as illustrative and not limiting.

The membrane may include additional components e.g. mediators, enzymes, cofactors, antibodies, reagents, and/or conducting particles, as well as incorporating a mixture of polymers (e.g. having ion exchange properties).

The membranes present in the sensor devices according to the invention are at least partially impermeable to charged non-lipophilic species and are selective by partitioning for lipophilic species. As such, the device may be used for the determination of a lipophilic component present in a sample. The lipophilic component of the sample may itself be directly detectable at the working electrode of the device. If however the component to be determined exhibits no or any insignificant electrochemical activity the membrane may incorporate means for interacting with the preselected component to produce a directly detectable electrochemically active species.

Although the permselective membrane is selective towards lipophilic species, we do not exclude the possibility of the sensor may also exhibit some degree of selectivity towards a small uncharged hydrophilic species such a hydrogen peroxide and quinones. As such the sensor may also be used for the detection of such small molecules. Furthermore, as mentioned above, it is also possible that the membrane may be used for the detection of charged species by virtue of the ion exchange properties of the charged organic species.

The types of analysis which may be effected with sensors in accordance with the invention includes, but are not limited to, those disclosed in PCT/GB92/00443.

It will be appreciated that for any particular type of analysis to be effected the composition of the membrane may be formulated to give optimum results. Thus, for example, if it is desired particularly to prevent negatively charged interferants passing across the membrane then the charged organic species may be a negative organic ion. This prevents the possibility of ion exchange between the (relatively large) charged organic species and the interferant. Similarly the use of an positively charged organic ion may be used to prevent interference by positively charged ions.

Figure 2:
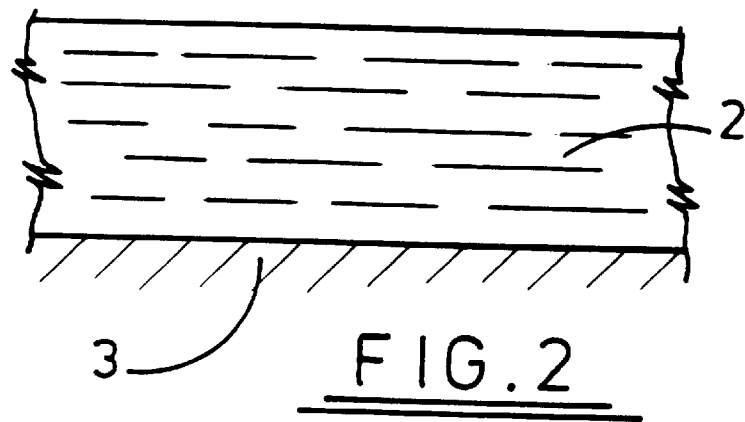
Figure 3:
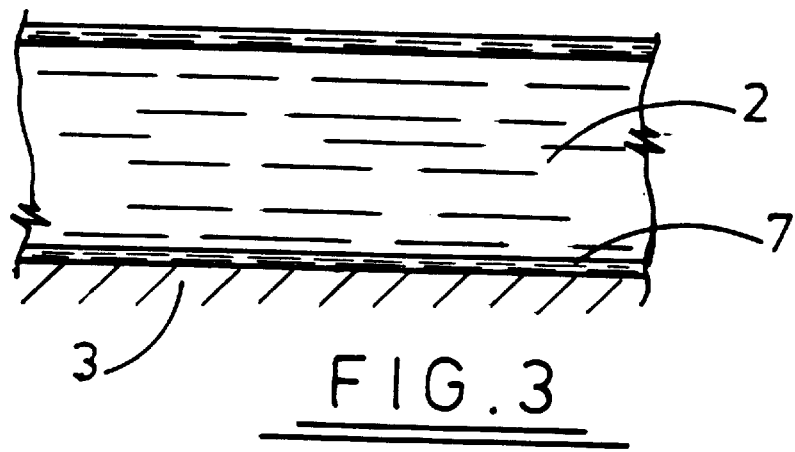

The invention will be further described, by way of example only, with reference to the accompanying drawings, in which:

FIG. 1 schematically illustrates one embodiment of the sensor device in accordance with the invention; and FIGS. 2 and 3 illustrate (to an enlarged scale) various membrane structures.

FIG. 1 illustrates a sensor device 1 for use in amprometric measurements. The device comprises a permselective membrane 2 in intimate contact with electrodes 3 and 4 mounted in a support 5. At its side opposite the support 5, the membrane 2 is in contact with bulk (analyte containing) solution 6 which may be aqueous or organic provided that it does not dissolve the membrane. It will be appreciated that the sensor may be disposable and intended for one measurement only, in which case the requirement is that the solution does not dissolve the membrane in the time scale of measurement.

Electrode 3 may be a working electrode (e.g. a platinum electrode) and electrode 4 may be a reference/pseudo reference electrode (e.g. of silver).

The membrane 2 may for example comprise polyvinyl chloride incorporating a charged organic species as described more fully above.

In use of the membrane, the polarisation of the electrodes and measurement of current in the cell is performed by appropriate amprometric methods. The provision of the organic charge carrier species in the membrane 2 provides for current flow between electrodes 3 and 4 without the need for a separate liquid or gel electrolyte layer being interposed between the electrodes and the membrane.

The membrane may be of the form illustrated in FIG. 2 in which all mobile species are retained within the polymer matrix. Alternatively the membrane may be as shown in FIG. 3 in which mobile species are present within the matrix of the polymer and also in a thin film 7 on the membrane surface which may result in the formation of a thin layer between membrane 2 and electrode 3 (and 4) during electrochemical cell construction.

Membranes for use in the sensor device may be produced by the following procedure which is given purely by way of example.

A membrane may be produced by dissolving PVC together with supporting electrolyte in tetrahydrofuran. Thus, for example, 0.06 g of PVC together with an appropriate amount of supporting electrolyte (see below) may be dissolved in 10 ml of tetrahydrofuran. The solution is poured into a 10 cm diameter petri dish, the lid replaced, and the tetrahydrofuran allowed to evaporate slowly at room temperature for 2–3 days.

The organic charged carrier species may be provided by 150 $\mu$l Aliquat 336 (tricaprylylmethyl ammonium chloride). The Aliquat 336 acts as both a charge carrier species and a plasticiser for the membrane.

Alternatively the charge carrier species may be provided by 35 mg of sodium tetrophenyl borate used in conjunction with 150 $\mu$l of isopropyl myristate which acts as plasticiser during membrane fabrication.

It will be appreciated from the foregoing description that the invention provides a number of advantages as set out below.

The sensor incorporates a simple construction of a membrane covered electrode using a single combined membrane/electrolyte layer.

The membrane covered electrode may be pre-polarised and conditioned with no liquid present.

The construction of the sensor device does not involve aqueous components. This avoids the need to lay down an aqueous layer which is an advantage if dry ingredients also need to be laid down.

The sensor device is able to exploit the advantages of organic phase electrochemistry e.g. wide applied voltage window, preconcentration effects and improvement in properties of any additional components related to the organic phase.

The membrane may be formulated to have a high degree of permselectivity (e.g. the use of a positively charged organic species will prevent positively charged interferants entering the membrane).

The absence of a separate liquid or gel phase electrolyte layer between the membrane and the electrodes avoids problems with diffusion control across such a layer.

There is reduced electrode fouling with real samples.

The invention renders possible the exploitation of thin/fragile membranes as intimate contact between the membrane and solid electrode serves as support.

We claim:

1. An amperometric sensor device for detecting a predetermined component present in a fluid sample and providing an output representative thereof, the device comprising a permselective membrane incorporating a charged organic species, said permselective membrane being selective, by partitioning, for lipophilic species, and an electrode arrangement having a working electrode and a reference/pseudo-reference electrode, said electrodes of the electrode arrangement being in intimate contact with the membrane but not being exposed at the side thereof to be presented to the fluid sample and wherein said charged organic species provides a conducting path through the membrane between said electrodes of the electrode arrangement.

2. The device as claimed in claim 1 wherein the membrane is of a synthetic polymer.

3. The device as claimed in claim 2 wherein the polymer is PVC.

4. The device as claimed in claim 2 wherein the membrane is plasticized.

5. The device as claimed in claim 4 wherein the plasticizer for the membrane is provided by the charged organic species.

6. The device as claimed in claim 1 wherein the charged organic species is provided by tricaprylylmethyl ammonium chloride.

7. The device as claimed in claim 1 wherein the charged organic species is provided by sodium tetraphenylborate.

8. The device as claimed in claim 1 wherein the membrane additionally incorporates at least one of a mediator, an enzyme, a cofactor, an antibody, a reagent, conducting particles, and a mixture of polymers.

9. The device as claimed in claim 1 wherein the electrode arrangement is in intimate contact with a face of the membrane.

10. The device as claimed in claim 1 wherein the electrodes are incorporated in the membrane.

* * * * *